(12) United States Patent
Beccaro et al.

(10) Patent No.: US 11,044,905 B2
(45) Date of Patent: Jun. 29, 2021

(54) TABLET WITH AN ANTIMYCOTIC AGENT, MEDICAL DEVICE AND METHOD FOR PRESERVING HARVESTED CORNEAS

(71) Applicant: ALCHILIFE S.R.L., Ponte San Nicolo (IT)

(72) Inventors: Mauro Beccaro, Cadoneghe (IT); Enrico Bettini, Fiesso d'Artico (IT); Paolo Signori, Verona (IT)

(73) Assignee: AL.CHI.MI.A. S.R.L., Ponte San Nicolo' (IT)

( * ) Notice: Subject to any disclaimer, the term of this patent is extended or adjusted under 35 U.S.C. 154(b) by 82 days.

(21) Appl. No.: 16/521,915

(22) Filed: Jul. 25, 2019

(65) Prior Publication Data

US 2020/0037605 A1 Feb. 6, 2020

(30) Foreign Application Priority Data

Aug. 3, 2018 (IT) .......................... 102018000007852

(51) Int. Cl.
| | |
|---|---|
| *A01N 1/02* | (2006.01) |
| *C08B 37/00* | (2006.01) |
| *A01N 43/90* | (2006.01) |
| *A61K 47/61* | (2017.01) |

(52) U.S. Cl.
CPC ........ *A01N 1/0215* (2013.01); *C08B 37/0069* (2013.01); *A01N 43/90* (2013.01); *A61K 47/61* (2017.08)

(58) Field of Classification Search
None
See application file for complete search history.

(56) References Cited

U.S. PATENT DOCUMENTS

| | | |
|---|---|---|
| 2013/0248480 A1 | 9/2013 | Perovitch |
| 2016/0220446 A1 | 8/2016 | Perovitch |
| 2016/0310600 A1 | 10/2016 | Ali et al. |

FOREIGN PATENT DOCUMENTS

| | | |
|---|---|---|
| EP | 2920295 B1 | 1/2017 |
| WO | 2016139619 A1 | 9/2016 |

OTHER PUBLICATIONS

Li Zhou et al: "Preparation, characterization, and evaluation of amphotericin B-loaded MPEG-PCL-g-PEI micelles for local treatment of oral *Candia albicans*", International Journal of Nanomedicine, vol. 12, Jun. 1, 2017, pp. 4269-4283.

*Primary Examiner* — Robert A Wax
*Assistant Examiner* — Randeep Singh
(74) *Attorney, Agent, or Firm* — Pearne & Gordon LLP

(57) ABSTRACT

A tablet containing at least amphotericin B deoxycholate, a substance with lubricating properties, a substance with disaggregating properties and a substance with aggregating properties, the tablet being usable in a device for preserving harvested corneas, in combination with a bottle (2) equipped with an openable and reclosable cap (7), where the bottle contains a sterile preserving liquid (3) having a pH of between 7.2 and 7.6 and wherein the tablet can be completely dissolved; in accordance with the method claimed, a harvested cornea being preservable in the preserving liquid in which the tablet has been dissolved, for up to at least 15 days at a temperature of between 2° C. and 10° C.

17 Claims, 1 Drawing Sheet

Figure 1:
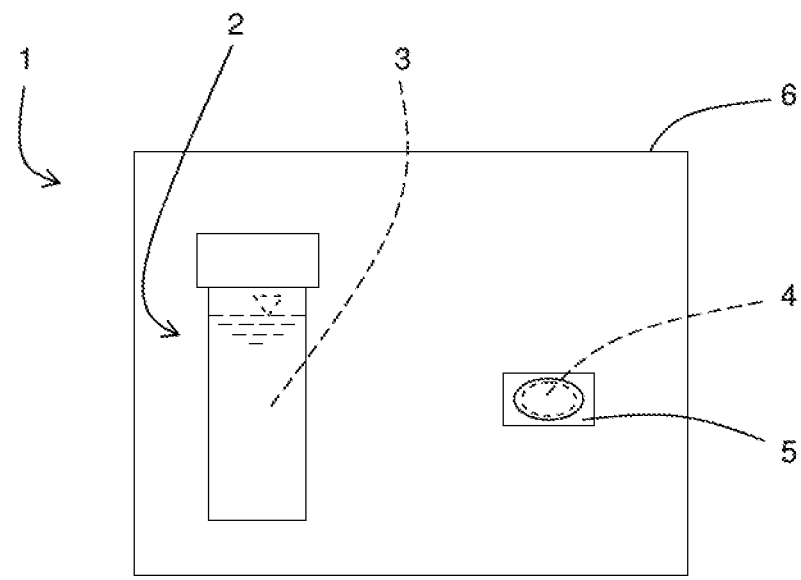

TABLET WITH AN ANTIMYCOTIC AGENT, MEDICAL DEVICE AND METHOD FOR PRESERVING HARVESTED CORNEAS

The present invention has been developed in the context of preserving harvested corneas, in the corneal transplantation sector, which is to say corneas removed from one donor subject with a view to their subsequent implantation in a subject other than the donor. The present invention therefore relates to a method of preserving harvested explanted corneas, as well as a tablet containing an antimycotic agent and a medical device, both of which have been conceived and developed as preferred tools for implementing the method.

As is known, two techniques are mainly used at present for preserving harvested corneas: low-temperature preservation and organ culture preservation.

In low-temperature preservation, preservation takes place at a nominal temperature of 4° C., whereas in organ culture preservation, preservation takes place at a nominal temperature of 31° C.

The main difference between the two methods resides in the differing temperature-related metabolisms both of the corneas themselves and of any pathogens that may be present.

This difference impacts both the formulation of the preserving liquids used in the two cases, and, consequently, their preservation methods.

In the case of organ culture preservation in particular, the preserving liquid must be provided both with a high quantity of nutrients and a relatively wide range of antibiotic substances that can counteract any bacterial infections.

In this regard, the main problems for organ culture preservation which have arisen over the years have concerned the need to introduce antibiotic substances with antifungal and antimycotic properties into the preserving liquid. The preferred option has been to use Amphotericin B, due to its known, efficacy. However, this substance is easily perishable and, under the conditions of use (31° C.), is unlikely to guarantee effective protection for periods longer than 14 days.

As preserving liquids are not extemporaneous preparations, but rather industrial products designed to have a medium-term market life (generally around two years from the manufacturing date), it became necessary to identify a method that preserved the preserving liquid before its use— from the moment amphotericin B is added to formulations— which was capable of guaranteeing the stability of amphotericin B until the moment of use.

The only solution used by preserving liquid producers until now for organ culture preservation has been to preserve the liquids themselves at a temperature of −20° C. until their use.

However, it is immediately evident that this option has a considerable impact in terms of costs, as it entails the need to ensure correct cold chain management from the moment of production until the moment it reaches the doors of the operating room in which the harvested cornea is to be inserted into the liquid.

Moreover, in the case of organ culture preservation, it would be advisable to always verify the activity of the amphotericin inside the preserving liquid before use to always verified before use in order to provide greater assurance to the subject who will receive the cornea (indeed, any—unknown—interruptions of the cold chain could have irreparably damaged the product). However, this desirable practice does not appear to be actually implemented at present, or at least not systematically.

At least until now, low-temperature corneal preservation has been a valid and simpler alternative to organ culture preservation.

Indeed, on the one hand the low metabolism of the cornea means that a smaller quantity of nutrients is required to be supplied via the preserving liquid, while on the other hand the similarly low metabolism of the bacteria means that fewer antibiotics can be used.

Indeed, until recently, for low-temperature preservation, the use of substances with antifungal or antimycotic properties in the preserving liquid, in particular amphotericin B, had never been considered necessarily. This allowed preserving liquids to be developed for low-temperature preservation which, before use, can be stored substantially at room temperature (indicatively between around 2° C. and 25° C., without any fear of temporary fluctuations outside this range) and transported from the place of production to the place of use, without therefore requiring excessive care in maintaining the appropriate temperatures (these liquids may also contain other types of antibiotic substances which do not vary the activity and/or useful life of the liquids at the temperatures indicated).

Recently, however, following applicant-conducted research in relation to the validation of methods for measuring the presence of bacterial contamination in harvested corneas intended for transplant (research that also led some patent applications to be filed last year), the applicant was able to ascertain that, in reality, it cannot be ruled out that fungal or mycotic infections could develop in corneas preserved at low temperatures.

In this context, the technical purpose of the present invention was to develop a method for preserving corneas at low temperatures which allowed any mycotic or antifungal infections to be effectively counteracted using industrially produced products.

Although it may have appeared desirable to also add amphotericin B to low-temperature cornea-preserving liquids to achieve this objective, the disadvantages linked to difficulties in guaranteeing the molecule's stability over time have led the applicant to rule out adopting a solution similar to that already adopted for organ culture preservation, and have instead encouraged the applicant to explore other options.

The technical purpose and the aims indicated above have ultimately been achieved by a method for preserving corneas at low temperatures according to the descriptions contained in the accompanying claims.

Furthermore, the achievement of these aims has been possible thanks to the development both of a tablet containing an antimycotic agent and of a medical device, also according to the descriptions contained in the accompanying claims.

Figure 2:
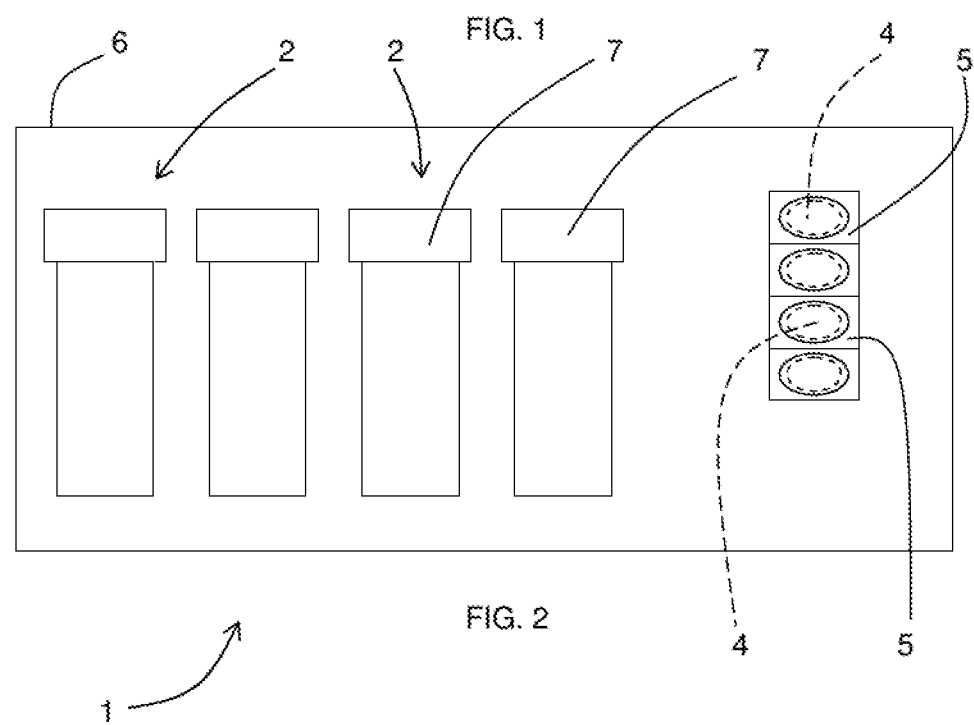

Further features and the advantages of the present invention will become more apparent after a careful reading of the following detailed description of several preferred, non-limiting embodiments of the several innovative aspects making up the present invention, some of which are shown in the accompanying figures, in which:

FIG. 1 shows a first embodiment of a medical device in accordance with an innovative aspect of this invention; and FIG. 2 shows a second embodiment of a medical device in accordance with an innovative aspect of this invention.

The innovative idea underlying the invention was to divide the preparation of the preserving liquid to be used for the preservation of the cornea into two steps: one production step for making the intermediate products (a step that can take place years before the actual use—following the tests carried out so far, we can guarantee a useful life of at least two years); and another step definable as the "commissioning" or "activation" step, in which the intermediate products are combined to produce the preserving liquid to be used (this second step should advantageously be performed just before the actual use—preferably a few minutes or a few hours before).

Described in greater detail, the idea underlying the present invention was to first produce a preserving liquid without amphotericin B, and to incorporate the right dose of amphotericin B via a solid tablet completely and quickly dissolvable in the preserving liquid. Indeed, it is known that, in its solid and properly preserved form, amphotericin B is stable over time and can guarantee a sufficient constancy of activity for at least a couple of years.

The first innovative aspect of the present invention therefore relates to the development of an innovative tablet comprising at least the following main components:
  amphotericin B deoxycholate;
  a substance with lubricating properties;
  a substance with disaggregating properties; and
  a substance with aggregating properties;

This tablet is preferably soluble in liquids that have a pH entirely within the range of between 7.2 and 7.6.

All of the substances listed above must be selected from those that are biocompatible with the corneas to be preserved. Furthermore, all substances selected are advantageously stable during gamma-ray sterilisation.

Advantageously, the tablet does not include other components, apart from any unavoidable impurities or water traces. Moreover, it is preferably free of effervescent substances.

In the preferred embodiments, the substance with lubricating properties is L-Leucine.

On the other hand, according to a first preferred solution for use, the substance with disaggregating properties and the substance with aggregating properties are both constituted of the same substance: isomalt.

According to a second solution for use, on the other hand, these are mannitol and sorbitol, respectively.

According to the preferred formulation, relative to the total weight of the tablet, amphotericin B deoxycholate is present in a quantity by weight of between 0.15% and 0.5%, and preferably between 0.25% and 0.4%, the substance with lubricating properties is present in a quantity of between 4% and 7%, and preferably between 5% and 6.5%, and the substances with disaggregating and aggregating quantities are present in a combined quantity of between 92.5% and 95.85%. Described in greater detail, according to the preferred formulations for the second solution for use described above, mannitol is present in a quantity by weight of between 10% and 12%, whereas sorbitol is present in a quantity by weight of between 80% and 85%.

As far as the production of the tablet is concerned, the currently preferred production method envisages the preparation of a hyper-concentrated solution of 1000× amphotericin B deoxycholate, using powdered amphotericin B as a foundation, followed by the freeze-drying of the amphotericin B deoxycholate. Subsequently, the freeze-dried powder is mixed with all other powdered substances so as to create as homogeneous a mixture as possible, which is subsequently compressed. The tablet thus obtained is inserted into the casing (blister) and gamma-ray sterilised at a dose of 25 KGy.

Depending on the demands and the production and/or commercial choices, the tablet constituting the first innovative aspect of the present invention can be used both in combination with known low-temperature preserving liquids and in combination with purpose-formulated liquids (such as that containing antibiotics described below).

According to a second innovative aspect of the present invention, the above-described tablet is envisaged to form part of a medical device 1 for preserving corneas at 4° C.

This medical device 1 first of all comprises a bottle 2 which contains a preserving liquid and which is provided with an operable and reclosable (preferably screw-on) cap 7. In the known way, the bottle 2 is advantageously made in such a way as to be functionable as a corneal container for the entire duration of preservation, and is initially sealed.

The preserving liquid 3 inside the bottle 2 is sterile and, in the known way, can contain various substances such as osmotic agents (e.g. dextran), energy sources (e.g. sodium pyruvate, glucose), nutrients (e.g. vitamins, mineral salts, amino acids), antibiotics (e.g. gentamicin), buffering agents (e.g. bicarbonate and HEPES) and a pH indicator (e.g. phenol red).

However, as regards the antibiotic substances in the preferred embodiments conceived in this invention, the preserving liquid 3 comprises streptomycin sulfate with a concentration of between 200 and 400 µg/ml, and gentamicin with a concentration of between 100 and 200 µg/ml.

As mentioned above, the second element of the medical device 1 is formed by a tablet 4 of the type described above, which is kept sterile in a suitable casing 5, such as a blister. The tablet 4 must be made in such a way as to be completely soluble at 4° C. in the quantity of preserving liquid 3 contained in the bottle 2.

Advantageously, both the tablet 4 inside the blister and the bottle 2 containing the preserving liquid 3 will have been gamma-ray sterilised, preferably once inserted inside the package 6 of the medical device 1. Alternatively, however, the tablet to be inserted inside the blister can be gamma-ray sterilised and a different sterilisation method can be used for the bottle (for instance, saturated steam for glass bottles).

Furthermore, the quantity ratios between the tablet 4 and the preserving liquid 3 are preferably such that the complete dissolving of the tablet 4 in the preserving liquid 3 leads there to be a concentration of amphotericin B deoxycholate in the preserving liquid 3 of between 1.5 and 25 advantageously between 3 and 12 µg/ml.

Moreover, the quantity ratios between the tablet 4 and the preserving liquid 3 are such that the preserving liquid 3, which initially has a pH of between 7.2 and 7.6, changes in pH by a maximum of ±0.2 after dissolving the tablet 4. Similarly, the quantity ratios between the tablet 4 and the preserving liquid 3 are preferably such that the preserving liquid 3, which initially has an osmolarity of 300±45 mOsm/kg, changes in osmolarity by a maximum of ±20 mOsm/kg after dissolving the tablet 4.

In the preferred embodiment, the bottle 2 contains between 15 and 30 ml of preserving liquid 3 (preferably 20 ml), and the tablet 4 has a weight of between 30 and 55 mg (advantageously 42 mg±3 mg).

In the preferred embodiment of the present invention, the tablet 4 is completely dissolvable in the preserving liquid 3, without the need for agitation, in a time of less than 30 minutes and preferably less than 20 minutes. Furthermore, the tablet 4 is preferably completely dissolvable in the preserving liquid 3, without the need for agitation, at any temperature between 2° C. and 25° C. However, the lower the temperature below ambient temperature, the longer the time required for complete dissolution (indicatively, however, the time will increase by a maximum of around 5-10 mins for the temperature range indicated).

In the context of the present description, ambient temperature means a temperature of between 18° C. and 25° C., preferably a temperature of 20° C.

Finally, the medical device 1 advantageously comprises a single package 6, which contains both the bottle 2 and the blister 5 containing the tablet 4, and which, once closed, is gamma-ray sterilised as described above.

FIG. 1 shows the simplest embodiment, in which a single bottle 2 and a single tablet 4 are present.

In general, however, the medical device 1 can comprise a plurality of bottles and a corresponding number of sterile tablets, as illustrated for instance in FIG. 2, where the package 6 contains four bottles and four tablets (each in its own blister 5).

Given that, when harvesting cornea, there are usually two corneas to be preserved, the medical device 1 can also advantageously comprise an even number of bottles with two tablets inserted together in a single blister 5.

The tablet 4 described in the present invention can be preserved in its blister 5 at a temperature of between 2° C. and 10° C. (preferably around 4° C.) for at least two years without significant variations in the activity of the amphotericin B deoxycholate. In turn, the preserving liquid 3 described above, containing gentamicin sulfate and streptomycin sulfate, must be preserved at a temperature of between 2° C. and 10° C., preferably at a temperature of around 4° C. The same is also self-evidently true of the medical device 1 of which it forms part. Nevertheless, momentary changes in temperature do not have significant effects on the activity of the two antibiotic molecules, which makes them considerably easier to preserve and transport than traditional organ culture liquids.

The medical device 1 and the above-described tablet 4 are used according to the third innovative aspect of the present invention; which is to say, the innovative method for preserving a harvested cornea.

It should be noted that this method can be implemented either by using the whole medical device described above or by using only the tablet 4 according to the present invention in combination with a generic bottle 2 containing a preserving liquid 3 with characteristics similar to those described above for the medical device 1.

Indeed, the method first of all envisages, for each cornea, taking a bottle 2 containing a preserving liquid 3, inserting a tablet 4 made according to the present invention into the bottle 2, and completely dissolving the tablet 4 in the preserving liquid 3. Advantageously, the preserving liquid 3 and the tablet 4 are initially sterile, and the steps of taking the bottle 2, inserting the tablet 4 in the bottle 2, and dissolving the tablet 4 are carried out in aseptic conditions. A bottle 2 should preferably be used that can be provided with a cap 7 which can be reclosed after inserting the tablet 4 until completely dissolved. The sterile tablet 4 is also preferably removed from a blister 5 under aseptic conditions.

In the preferred embodiment, the step of dissolving the tablet 4 in the preserving liquid 3 is carried out, without agitation, preferably leaving the bottle 2 stationary, at a temperature of between 2° C. and 25° C. Preferably, however, this is carried out at ambient temperature and has a duration of less than 30 minutes, and preferably less than 20 minutes. However, once dissolution is complete, a step of agitating the preserving liquid 3 is preferably carried out so as to make the preserving liquid 3, to which the substances previously contained in the tablet 4 have been added, as homogeneous as possible.

At this point, the method envisages inserting the cornea to be preserved in the bottle 2 by immersing it in the preserving liquid 3 in which the tablet (4) has been dissolved, closing the bottle 2 and, finally, preserving the bottle 2, with the cornea inside, at a temperature of between 2° C. and 10° C. (preferably around 4° C.).

The tests so far conducted have shown that it is thus possible to obtain optimal preservation of the cornea at least for a duration of less than or equal to 15 days. Indeed, the comparative tests carried out have shown neither any preservation differences compared to the use of known preserving liquids nor any negative effect on the corneas.

Further tests carried out have also shown that using preserving liquid 3 in which the tablet 4 has been dissolved allows 105 cfu/*Candida albicans* tissue to be eliminated after 10 days of incubation at 4° C.

The present invention therefore offers significant advantages.

Finally, it is worth noting that the present invention is relatively easy to make and that the cost associated with its implementation is also not very high.

Many modifications and variations can be made to the invention as designed herein without departing from the scope of the present invention.

All details can be replaced by other technically equivalent details and any materials, shapes and dimensions of the various components may be used according to requirements.

The invention claimed is:

1. A tablet comprising:
    amphotericin B deoxycholate in a quantity of between 0.15% and 0.5% by weight;
    L-Leucine in a quantity of between 4% and 7% by weight; and
    mannitol and sorbitol, together, in a quantity of between 92.5% and 95.5% by weight;
    wherein all quantities are relative to the total weight of the tablet, and wherein the tablet is soluble in a liquid having a pH of between 7.2 and 7.6.

2. The tablet according to claim 1, wherein the amphotericin B deoxycholate is present in a quantity of between 0.25% and 0.4% by weight, relative to the total weight of the tablet.

3. The tablet according to claim 1, wherein the L-Leucine is present in a quantity of between 5% and 6.5% by weight, relative to the total weight of the tablet.

4. The tablet according to claim 1, wherein the mannitol is present in a quantity of between 10% and 12% by weight, relative to the total weight of the tablet.

5. The tablet according to claim 1, wherein the sorbitol is present in a quantity of between 80% and 85% by weight, relative to the total weight of the tablet.

6. A tablet comprising:
    amphotericin B deoxycholate in a quantity of between 0.15% and 0.5% by weight;
    L-Leucine in a quantity of between 4% and 7% by weight; and
    isomalt in a quantity of between 92.5% and 95.5% by weight;
    wherein all quantities are relative to the total weight of the tablet, and wherein the tablet is soluble in a liquid having a pH of between 7.2 and 7.6.

7. A medical device for preserving a cornea at a temperature of between 2° C. and 10° C. comprising:
    a bottle containing a sterile preserving liquid, wherein the bottle comprises:
    a cap; and
    a blister containing a tablet according to claim 1 or 6;

wherein the tablet is sterile, wherein the tablet is completely dissolvable in the preserving liquid without agitation and within a duration of less than 30 minutes at a temperature of between 18° C. and 25° C., and wherein the complete dissolving of the tablet in the preserving liquid imparts a concentration of amphotericin B deoxycholate in the preserving liquid of between 1.5 μg/ml and 25 μg/ml.

8. The medical device according to claim 7, wherein the complete dissolving of the tablet in the preserving liquid imparts a concentration of amphotericin B deoxycholate in the preserving liquid of between 3 μg/ml and 12 μg/ml.

9. The medical device according to claim 7, wherein the pH of the preserving liquid is between 7.2 and 7.6 before the complete dissolving of the tablet, and wherein the pH of the preserving liquid changes by a maximum of 0.2 after the complete dissolving of the tablet.

10. The medical device according to claim 7, wherein the bottle contains between 15 ml and 30 ml of the preserving liquid, and wherein the tablet has a weight of between 30 mg and 55 mg.

11. The medical device according to claim 7, wherein the preserving liquid further comprises streptomycin sulfate at a concentration of between 200 μg/ml and 400 μg/ml, and gentamicin at a concentration of between 100 μg/ml and 200 μg/ml.

12. The medical device according to claim 7, further comprising one or more of the bottle and one or more of the tablet, wherein the total number of the bottles and the total number of the tablets is the same.

13. A method for preserving a harvested cornea comprising:
providing a bottle containing a preserving liquid;
inserting in the bottle a tablet according to claim 1 or 6;
dissolving the tablet in the preserving liquid;
inserting the harvested cornea in the preserving liquid in which the tablet has been dissolved;
closing the bottle; and
storing the bottle at a temperature of between 2° C. and 10° C.

14. The method according to claim 13, wherein the preserving liquid and the tablet are sterile prior to the inserting of the tablet in the bottle, and wherein the providing of the bottle containing the preserving liquid, the inserting of the tablet in the bottle, and the dissolving of the tablet in the preserving liquid are performed in asepsis.

15. The method according to claim 13, wherein the dissolving of the tablet in the preserving liquid is performed without agitation; and wherein after the dissolving of the tablet in the preserving liquid and before the inserting of the harvested cornea in the preserving liquid, the preserving liquid is agitated.

16. The method according to claim 13, wherein the dissolving of the tablet in the preserving liquid is performed at a temperature of between 2° C. and 25° C., or at ambient temperature.

17. The method according to claim 13, wherein the storing of the bottle is performed for a duration of less than or equal to 15 days.

* * * * *